United States Patent [19]

Rosik

[11] Patent Number: 5,616,312

[45] Date of Patent: Apr. 1, 1997

[54] THIOL LIGANDS AND COMPLEXES FOR X-RAY IMAGING

[75] Inventor: Leonard O. Rosik, Troy, Mo.

[73] Assignee: Mallinckrodt Medical, Inc., St. Louis, Mo.

[21] Appl. No.: 402,423

[22] Filed: Mar. 10, 1995

[51] Int. Cl.$^6$ ............................ A61B 5/055; C07F 9/94
[52] U.S. Cl. ........................ 424/9.364; 424/9.365; 436/173; 514/492; 514/503; 534/15; 534/16; 556/57; 556/61; 556/63; 556/64; 556/77; 556/81; 556/107; 562/556
[58] Field of Search ............................. 534/16, 15; 556/1, 556/61, 63, 57, 64, 77, 81, 107; 424/9.364, 9.365; 436/173; 514/492, 503; 562/556; 564/153, 154, 194, 500

[56] References Cited

U.S. PATENT DOCUMENTS

| | | | |
|---|---|---|---|
| 5,314,680 | 5/1994 | Rajagopalan et al. | 424/9 |
| 5,463,030 | 10/1995 | Subramanian et al. | 534/16 |
| 5,466,438 | 11/1995 | Unger et al. | 424/9.365 |
| 5,466,439 | 11/1995 | Gibby et al. | 424/9.365 |
| 5,466,878 | 11/1995 | Junino et al. | 564/197 |
| 5,476,644 | 12/1995 | Illig et al. | 424/1.11 |

*Primary Examiner*—Porfirio Nazario-Gonzalez
*Attorney, Agent, or Firm*—Brian K. Stierwalt

[57] ABSTRACT

The present invention provides new and structurally diverse compositions comprising compounds of the general formula:

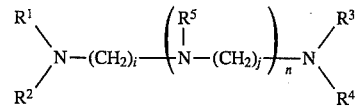

Wherein $R^1$, $R^2$, $R^3$, $R^4$, and $R^5$ are the same or different and are —CO—$(CH_2)_y$—SH, —$(CH_2)_2$—SH, —$SO_2$—$(SH_2)_t$—SH,—SH,—$(CH_2)_q$—COOH, and —$(CH_2)_v$—$CONR^6R^7$, provided at least one of $R^1$, $R^2$, $R^3$, $R^4$ and $R^5$ is a sulfur containing moiety; n is 0 to about 10; i is 2 to about 5; j is 2 to about 5; y is 1 to about 5; z is 1 to about 6; t is 1 to about 5; q is 1 to about 5; v is 1 to about 5; $R^6$ is H, alkyl, hydroxyalkyl, polyhydroxyalkyl, arylalkyl or alkoxyalkyl; $R^7$ is H, alkyl, hydroxyalkyl, polyhydroxyalkyl, arylalkyl or alkoxyalkyl; and $R^7$ can be polyamine when $R^6$ is H.

Methods for imaging using compositions of the invention are also provided.

7 Claims, No Drawings

THIOL LIGANDS AND COMPLEXES FOR X-RAY IMAGING

FIELD OF THE INVENTION

This invention relates to X-ray imaging. More particularly the invention relates to methods and compositions for enhancing X-ray imaging.

BACKGROUND OF THE INVENTION

The search for ideal contrast media for X-ray radiodiagnostic studies has extended over many decades. Bismuth subnitrate was the first radiocontrast agent used for visualization of the alimentary tract. Later, barium sulfate, a safer agent, was introduced. Barium sulfate has remained the most widely used radiographic agent for the alimentary tract (W.H. Strain, International Encyclopedia of Pharmacology and Therapeutics, Section 76, Vol. 1, Radiocontrast Agents, Chapter 1, Historical Development of Radiocontrast Agents, 1971, Pergamon Press). The inorganic, insoluble oral agents like bismuth subnitrate and barium sulfate serve as valuable tools for gastrointestinal radiodiagnosis.

Unlike gastrointestinal radiodiagnosis, urographic and angiographic X-ray procedures, require intravascular administration of a safe, water-soluble, radiopaque contrast medium. Since the introduction of the water-soluble ionic triiodobenzoic acid derivatives, such as diatrizoic acid and iothalamic acid, in the early 1960's, radiographic visualization of the vascular system has become the most important application of X-ray contrast media. These X-ray procedures are valuable in the diagnosis and evaluation of a variety of diseases that involve or cause alterations in normal vascular anatomy or physiology.

In the last ten to fifteen years a major advancement in the area of triiodobenzene X-ray contrast media has been the development of nonionic agents. The main reason for a nonionic radiological composition is to eliminate sensations of pain and warmth caused by the high osmolality associated with the ionic nature of triiodobenzoic acid derivatives. Safer and superior nonionic triiodobenzoic acid derivatives such as iopamidol, iohexol and ioversol have been commercially introduced. Because of their improved chemical structures, which when in solution provide lower osmolality, nonionic agents provide greater patient comfort. Adverse reactions, especially in the sensation of pain, warmth, and hemodynamic effects are greatly reduced when nonionic agents are used.

An ideal intravascular X-ray contrast agent should possess many desirable properties. Some of the most important properties are: 1) maximum X-ray opacity; 2) biological safety; 3) high water solubility; 4) stability; 5) low osmolality; and 6) low viscosity. Therefore, in order to obtain these properties, X-ray contrast agents result in complex molecules.

Iodine is used in triiodobenzene derivative compounds to provide opacification to X-rays. The remaining portion of the molecule provides the means for safe transport of the iodine atoms through the body. The structural makeup of the molecule is critical in providing stability, solubility and other desirable physiochemical properties and biological safety of the contrast agent.

There is a continuing need for agents which substantially meet the desirable properties of an intravascular X-ray contrast agent.

SUMMARY OF THE INVENTION

The present invention provides new and structurally diverse compositions Comprising compounds of the general formula:

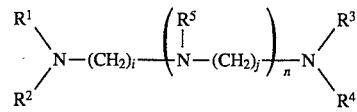

Wherein $R^1$, $R^2$, $R^3$, $R^4$, and $R^5$ are the same or different and are $-CO-(CH_2)_y-SH$, $-(CH_2)_2-SH$, $-SO_2-(SH_2)_t-SH$, $-(CH_2)_q-COOH$, and $-(CH_2)_v-CONR^6R^7$, provided at least one of $R^1$, $R^2$, $R^3$, $R^3$, and $R^4$ is a sulfur containing moiety; n is 0 to about 10; i is 2 to about 5; J is 2 to about 5; y is i to about 5; z is 1 to about 6; t is 1 to about 5; q is i to about 5; v is 1 to about 5; $R^6$ is H, alkyl, hydroxyalkyl, polyhydroxyalkyl, arylalkyl or alkoxyalkyl; $R^7$ is H, alkyl, hydroxyalkyl, polyhydroxyalkyl, arylalkyl or alkoxyalkyl; and $R^7$ can be polyamine when $R^6$ is H.

Also provided are compositions comprising complexes of the compounds with metal ions of the general formula:

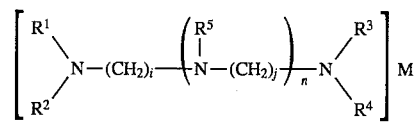

Wherein $R^1$, $R^2$, $R^3$, $R^4$, and $R^5$ are the same or different and are $-CO-(CH_2)_y-SH$, $-(CH_2)_2-SH$, $-SO_2-(SH_2)_t-SH$, $-(CH_2)_q-COOH$, and $-(CH_2)_v-CONR^6R^7$, provided at least one of $R^1$, $R^2$, $R^3$, $R^4$ and $R^5$ is a sulfur containing moiety; n is 0 to about 10; i is 2 to abut 5; j is 2 to about 5; y is 1 to about 5; z is 1 to abut 6; t is 1 to about 5; q is 1 to about 5; v is 1 to about 5; $R^6$ is H, alkyl, hydroxyalkyl, polyhydroxyalkyl, arylalkyl or alkoxyalkyl; $R^7$ is H, alkyl, hydroxyalkyl, polyhydroxyalkyl, arylalkyl or alkoxyalkyl; and $R^7$ can be polyamine when $R^6$ is H; and M is lead, bismuth, gadolinium, dysprosium, holmium, tungsten, or praseodymium.

Compositions comprising the above formulas wherein M is a metal ion capable of absorbing x-rays are also provided for use as x-ray contrast agents.

Diagnostic compositions comprising the compounds of the invention are also provided. Methods of performing diagnostic procedures with compositions of the invention are also disclosed. The methods comprise administering to a patient an effective amount of the compositions of the invention and optionally subjecting the patient to an imaging procedure of imaging.

DETAILED DESCRIPTION

The compositions of the invention are suitable for use with x-ray imaging modalities.

Examples of suitable alkyl groups for use with the invention include methyl, ethyl, propyl, isopropyl, butyl, cyclohexyl, heptyl and octyl. Suitable alkoxy groups include methoxy, ethoxy, propoxy, butoxy, pentoxy, hexoxy, heptoxy and octoxy. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris(hydroxymethyl)methyl and 2-hydroxy-1-hydroxymethyl-ethyl. Suitable alkoxyalkyl groups include methoxymethyl, 2,3-dimethoxypropyl, tris (methoxymethyl)methyl, and 2-methoxy-1-methoxymethyl-ethyl. The hydroxyalkyl groups and alkoxyalkyl groups increase water solubility. Arylalkyl groups include phenylmethyl and phenylpropyl. Polyamines include polylysine, serum albumin, and diethylene triamine. Elements suitable for use with the invention include those with atomic numbers 42 through 86. The $R^1$ through $R^5$ groups are designed as metal ligating moieties. Polyamine type molecules are believed to increase amplification and x-ray opacity by making binding of more metal atoms obtainable. The amino alkylaline repeating unit depicted in the structure may be the same or different as it repeats.

Examples of suitable compounds of the invention are:

N,N-bis(3-thiopropyl)-N'-carboxymethyl-N'-(2,3-dihydroxypropyl-amino-carbonylmethyl)-1,2-diaminoethane dihydrobromide;

N,N-bis (2-thioethyl)-N'-carboxymethyl-N'-(2,3-dihydroxypropyl-amino-carbonylmethyl)-1,3-diaminopropane dihydrobromide;

N,N-bis (3-thiopropyl)-N'-carboxymethyl-N'-(2,3-dihydroxypropyl-amino-carbonylmethyl)-1,3-diaminopropane dihydrobromide;

1,1,4-tris(2-thioethyl)-7,7-bis(2',3'-dihydroxypropylaminocarbonylmethyl-1,4,7-triazaheptane trihydrobromide;

1,1,4-tris(2-thiopropyl)-7,7-bis(2',3'-dihydroxypropylaminocarbonylmethyl)-1,2-triazaheptane trihydrobromide; and N,N-bis(2-thioethyl)-N'-carboxymethyl-N'-(2,3-dihydroxypropylaminocarbonylmethyl)-1,2-diaminoethane dihydrobromide.

Examples of preferred comounds for X-ray contrast include:

The metal complex of N,N-bis (3-thiopropyl)-N'-carboxymethyl-N'-(2,3-dihydroxypropyl-amino-carbonylmethyl) -1,2-diaminoethane;

The metal complex of N,N-bis (2-thioethyl)-N'-carboxymethyl-N'-(2,3-dihydroxypropylamino-carbonylmethyl) -1,3-diaminopropane;

The metal complex of N,N-bis (3-thiopropyl)-N'-carboxymethyl-N'-(2,3-dihydroxypropyl-amino-carbonylmethyl) -1,3-diaminopropane;

The metal complex of 1,1,4-tris(2-thioethyl)-7,7-bis(2',3'-dihydroxypropylaminocarbonylmethyl)-1,4,7-triazaheptane;

The metal complex of 1,1,4-tris(2-thiopropyl)-7,7-bis(2',3'-dihydroxypropylaminocarbonylmethyl)-1,4,7-triazaheptane; and The metal complex of N,N-bis(2-thioethyl)-N'-carboxymethyl-N'-(2,3-dihydroxypropylaminocarbonylmethyl)-1,2-diaminoethane.

For use as X-ray contrast applications the complexed metal ion must be able to absorb adequate amounts of the X-rays. These metal ions are generally referred to as radiopaque. Suitable elements for use as the radiopaque metal ion include lead, bismuth, gadolinium, dysprosium, holmium, tungsten and praseodymium.

The compositions of the invention can be formulated into therapeutic or diagnostic compositions for enteral or parenteral administration. These compositions contain an effective amount of the metal complex along with conventional pharmaceutical carriers and excipients appropriate for the type of administration contemplated. For example, parenteral formulations advantageously contain a sterile aqueous solution or suspension of from about 0.05 to about 1.0M of a metal complex according to this invention. Parenteral compositions may be injected directly or mixed with a large volume parenteral composition for systemic administration. Preferred parenteral formulations have a concentration of metal complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, non-toxic cation. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the metal complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the image. Such doses may vary widely, depending upon the particular paramagnetic ion complex employed, the organs or tissues which are the subject of the imaging procedure, the imaging procedure, the imaging equipment being used, and the like. In general, parenteral dosages will range from about 0.001 to about 1.0 mMol of metal ion complex per kg of patient body weight. Preferred parenteral dosages range from about 0.01 to about 0.5 mMol of metal ion complex per kg of patient body weight. Enteral dosages generally range from about 0.5 to about 100 mMol, preferably from about 1.0 to about 20 mMol, more preferably from about 1.0 to about 10.0 mMol of metal ion complex per kg of patient body weight.

The diagnostic compositions of the invention are used in the conventional manner. The compositions may be administered to a patient, typically a warm-blooded animal, either systemically or locally to the organ or tissue to be imaged, and the patient then subjected to the imaging procedure.

X-ray contrast Imaging Procedures are found in Albert A. Moss, M. D., Gordon Gamsu, M. D., and Harry K. Genant, M. D., *Computed Tomography of the Body*, (W. B. Saunders Company, Philadelphia, Pa. 1992) and M. Sovak, Editor, *Radiocontrast Agents*, (Springer-Verlag, Berlin 1984 ).

General procedures for ligand synthesis and metal complexing are well known and exemplified in such texts as Watson, A.D., Rocklage, S. C., Carvlin, M. J. In Magnetic Resonance Imaging, 2nd ed.; Stark, D. D., Bradley, W. G., Eds.; Mosby Year Book: St. Louis, Mo, 1992, Chapter 14 and Gaughan, G. In Enhanced Magnetic Resonance Imaging, Runge, V. M., Ed.; Mosby Year Book: St. Louis, Mo., 1989, Chapter 9.

The following examples illustrate the specific embodiments of the invention described in this document. As would be apparent to skilled artisans, various changes and modifications are possible and are contemplated within the scope of the invention described.

EXAMPLES

Example 1

N,N-Di-(2-thieothyl)-N-'-carboxylmethyl-N'-(2,3-dihydroxy-propylaminocarbonylmethyl)-1,2-diaminoethane Dihydrobromide (7):

A. 2-(p-Methoxybenzylthio)ethanol (1) :.

To a solution of mercaptoethanol (8.6 g, 7.7 ml, 0.11 mol) and potassium hydroxide (6.2 g, 0.11 mol) in 250 ml of ethanol is added p-methoxybenzyl chloride (15.66 g, 13.6 ml, 0.1 mol) in approximately 2 ml portions over 2 minutes. The mixture is stirred at room temperature for 4 hours. The mixture is acidified to pH 4 with 1M hydrochloric acid and the ethanol removed en vacuo. The residue is dissolved in 200 ml of methylene chloride and the water layer separated. The water layer is extracted twice with 25 ml of methylene chloride. The combined methylene chloride layers are washed twice with 100 ml of 5% sodium bicarbonate and once with 100 ml of brine. The methylene chloride solution is dried over magnesium sulfate, filtered, and the solvent removed en vacuo to give an oil. The oil is vacuum distilled and a yield of 70 to 80% is obtained.

B. 2-(p-Methoxybenzylthio)ethyl Bromide (2):

To a cold (0° C.) solution of 2-(p-methoxybenzylthio)ethanol (14.87 g, 0.075 mol) in 200 ml of methylene chloride is added a solution of phosphorous tribromide (8.1 g, 2.85 ml, 0.030 mol) in 50 ml of methylene chloride over 30 minutes. The mixture is stirred at 0° C. for 1 hour and then warmed to room temperature and stirred an additional 3 hours. A solution of sodium bicarbonate (8.4 g, 0.1 mol) in 200 ml of water is added dropwise over 1 hour. The layers are separated and the water layer extracted with 50 ml of methylene chloride. The combined methylene chloride layers are washed with 100 ml of brine, dried over magnesium sulfate, filtered, and the solvents are removed en vacuo. The resulting oil can be vacuum distilled and a yield of 70 to 80% is obtained.

C. N,N-Di-(2-(p-methoxybenzylthio)ethyl)amine Hydrochloride (3):

To a stirring 60° C. solution of tosylamide (4.3 g, 0. 025 mol) and potassium carbonate (13.8 g, 0.1 mol) in 100 ml of dimethylformamide (DMF) is added dropwise a solution of 2-(p-methoxybenzylthio)ethyl bromide (14.4 g, 0.055 mol) in 50 ml of DMF over 6 hours. The mixture is stirred for 24 to 48 hours at the existing temperature. The solvent is removed en vacuo and the residual oily solid partitioned between 200 ml of water and 100 ml of methylene chloride. The layers are separated, and the water layer extracted three times with 50 ml of methylene chloride. The combined extracts are washed twice with 100 ml of 0.5N Hydrochloric acid, 100 ml of water, 100 ml of brine, and dried over sodium sulfate. The resulting methylene chloride solution is stirred at 0° C. and a tetrahydrofuran (THF) solution of samarium iodide (0.030 mol) is added dropwise over one hour. The resulting mixture is allowed to warm to room temperature over two hours. The mixture is extracted twice with 50 ml of 1M Hydrochloric acid. The combined acid extracts are washed twice with methylene chloride. The hydrochloric acid is removed en vacuo. The material can be recrystallized from ethyl acetate/ether. The yield is 85 to 95%.

D. N,N-Bis(t-Butyloxycarbonylmethyl)-2-bromoethylamine (4):

To a solution of t-butyl bromoacetate (100 g, 0.513 mol), potassium bicarbonate (57 g, 0.57 mol) in 370 ml of dimethylformamide at 0° C. under argon was added a solution of ethanolamine (13.9 g, 0.228 mol) in 30 ml of dimethylformamide over 15 minutes. After the addition was complete the addition funnel was washed twice with 2 ml of dimethylformamide. The reaction mixture was stirred at 0° C. for one hour and then the ice bath was removed, allowing the reaction mixture to warm to room temperature. The mixture was stirred at room temperature under argon for 22 hours. The mixture was partitioned between 700 ml of methylene chloride and 700 ml of saturated sodium bicarbonate solution. The layers were separated and the organic phase washed again with 700 ml of saturated sodium bicarbonate. The combined aqueous layers were extracted twice with 200 ml of methylene chloride. The combined methylene chloride extracts were washed with 500 ml of brine, dried over magnesium sulfate, and filtered. The solvent was removed en vacuo to give an oil. This material was dissolved in 600 ml of methylene chloride. In this solution was dissolved triphenyl phosphine (65.8 g, 0.251 mol). The solution was cooled to 0° C. and solid N-bromosuccinimide (44.7 g, 0.251 mol) was added portion wise over 5 minutes, and washed with two 50 ml portions of methylene chloride. The solution was stirred 1.5 hours at 0° C. The solvent was removed en vacuo and the resulting semisolid residue triturated three times with 500 ml of ether. The solid was filtered and the ether solution was concentrated to approximately 100 ml and filtered. The filtrate was percolated through a column of silica, eluting with additional ether. The ether was removed en vacuo, and gave an oil. The material was purified by chromatography on silica with 9:1 hexane:ether. The yield was 55 to 65%.

E. N,N-Di-(2-(p-methoxybenzylthio)ethyl)-N',N'-Bis-(t-Butyloxycarbonylmethyl)-1,2-diaminoethane (5) :

To a stirring solution of

E. N,N-di-(2-(p-methoxybenzylthio)ethyl)amine hydrochloride (8.3 g, 0.02 mol) in 200 ml of acetonitrile is added diisopropylethylamine (6.5 g, 0.05 mol). To this mixture is added a solution of N,N-bis(t-butyloxycarbonylmethyl)-2-bromoethylamine (17.6 g, 0.05 mol) in 100 ml of acetonitrile. The mixture is stirred overnight at room temperature. The solvent is removed en vacuo and the remaining material partitioned between 200 ml of methylene chloride and 200 ml of 5% sodium bicarbonate solution. The layers are separated, and the methylene chloride layer is washed with 200 ml of 5% sodium bicarbonate, 200 ml of water, and 200 ml of brine. The solution is dried over sodium sulfate and the solvent removed en vacuo to give a solid that can be purified by chromatography on silica with methylene chloride/methanol. The yield is 80 to 90%.

F. N,N-Di-(2-(p-methoxybenzylthio)ethyl)-N',N'-dicarboxylmethyl-1,2-diaminoethane (6):

To a solution of potassium hydroxide (5.6 g, 0.10 mol) in 200 ml of 50% aqueous ethanol is added N,N-di-(2-(p-methoxybenzylthio)ethyl)-N',N'-bis-(t-butyloxy-carbonylmethyl)-1,2-diaminoethane (6.5 g, 0.01 mol) with stirring. The mixture is refluxed gently for 4 hours and then cooled to room temperature. The pH of the solution is adjusted to 7 with 6M hydrochloric acid. The volume of the solution was reduced by one half en vacuo, and then the solution was diluted with 100 ml of water. The mixture is extracted five times with 50 ml of methylene chloride. The extracts are washed once with 100 ml of brine, dried over sodium sulfate, and the solvent removed en vacuo. The yield is 70 to 80%.

G. N,N-Di-(2-thioethyl)-N'-carboxylmethyl-N'-(2,3dihydroxypropylaminocarbonylmethyl)-1,2-diaminoethane Dihydrobromide (7):

To a stirring solution of N,N-di-(2-(p-methoxybenzylthio)ethyl)-N',N'-dicarboxylmethyl-1,2diaminoethane (2.7 g, 5 mmol) in 50 ml of methylene chloride is added in one portion a solution of dicyclohexylcarbodiimide (1.13 g, 5.5 mmol) in 10 ml of methylene chloride. The mixture is stirred overnight at room temperature. The solid is removed by vacuum filtration and the solid washed three times with 10 ml of methylene chloride. The solvent is removed en vacuo and gives an oil that is picked up in 100 ml of acetonitrile at room temperature. A solution of aminopropanediol acetonide (0.72 g, 5.5 mmol) in 10 ml of acetonitrile is added and the mixture stirred at room temperature overnight. The solvent is removed en vacuo and gives an oil. The material is picked up in 100 ml of methylene chloride and cooled to 0° C. under nitrogen. To this mixture is added 50 ml of trifluoroacetic acid. Then triethylsilane (1.74 g, 15 mmol) is added, and the mixture stirred at the existing temperature for 4 hours. The volatiles are removed en vacuo and a solution of 10 ml of concentrated hydrobromic acid and 40 ml of absolute ethanol is added. On sitting at 0° C., a white solid forms which is vacuum filtered, washed with 10 ml of cold absolute ethanol, and dried under vacuum. The yield is 50 to 60%.

Example 2

A. The Bismuth Complex of N,N-Bis(2-thioethyl)-N'-carboxymethyl-N'-(2,3-dihydroxypropylaminocarbonyl-methyl)-1,2-diaminoethane (8):

The N,N-bis(2-thioethyl)-N'-carboxymethyl-N'-(2,3-dihydroxypropylaminocarboxymethyl)-1,2-diaminoethane dihydrobromide from Example 1G (2.66 g, 5 mmol) is stirred with 200 ml of 95% ethanol under argon. To this is added a solution of bismuth chloride (1.58 g, 5 mmol) in 20 ml of 4M hydrochloric acid over 1 minute. Stir the mixture for 30 minutes. Adjust the pH of the mixture to 4 with 6M sodium hydroxide solution. Cool the mixture with a room temperature water bath during the neutralization. Vacuum filter the solid and wash three times with 20 ml of 85% ethanol. The complex is purified by flash chromatography on RP-18 using ethanol and water. The yield is 60 to 70%.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A method of imaging comprising administering to a patient a compound of the general formula:

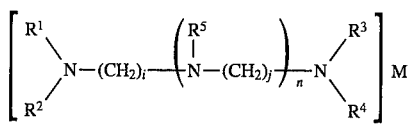

Wherein $R^1$, $R^2$, $R^3$, $R^4$, and $R^5$ are the same or different and are —CO—$(CH_2)_y$—SH, —$(CH_2)_2$—SH, $(CH_2)_3$—SH —, $(CH_2)_q$—COOH, and —$(CH_2)_v$ —$CONR^6R^7$, provided at least one of $R^1$, $R^2$, $R^3$, $R^4$ and $R^5$ is a sulfur containing moiety; n is 0 to about 10; i is 2 to about 5; J is 2 to about 5; y is 1 to about 5; z is 1 to about 6; t is 1 to about 5; q is 1 to about 5; v is 1 to about 5; $R^6$ is H, alkyl, hydroxyalkyl, polyhydroxyalkyl, arylalkyl or alkoxyalkyl; $R^7$ is H, alkyl, hydroxyalkyl, polyhydroxyalkyl, arylalkyl or alkoxyalkyl; and $R^7$ can be polyamine when $R^6$ is H; and M is lead, bismuth, gadolinium, dysprosium, holmium, tungsten, or praseodymium.

2. The method of claim 1 wherein the compound has the general formula:

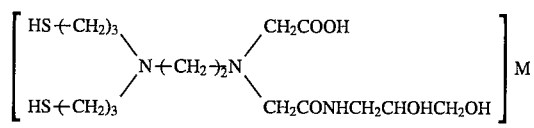

Wherein M is bismuth.

3. The method of claim 1 wherein the compound has the general formula:

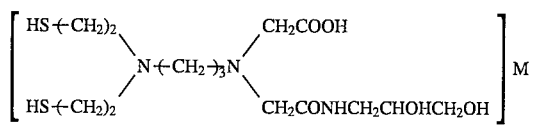

Wherein M is bismuth.

4. The method of claim 1 wherein the compound has the general formula:

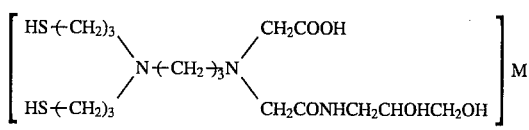

Wherein M is bismuth.

5. The method of claim 1 wherein the compound has the general formula:

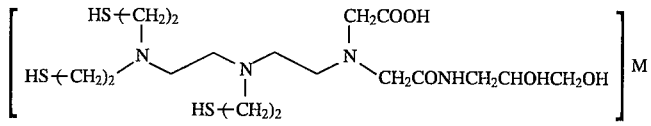

Wherein M is bismuth.

6.. The method of claim 1 wherein the compound has the general formula:

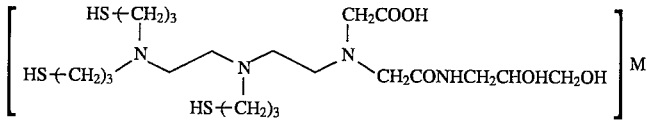

Wherein M is bismuth.

7. The method of claim 1 wherein the compound has the general formula:

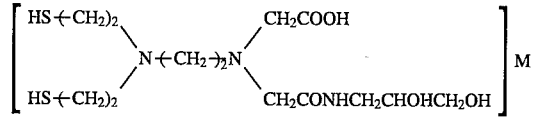

Wherein M is bismuth.

* * * * *